(12) United States Patent
Kleinman Ben Tsvi et al.

(10) Patent No.: US 12,226,349 B2
(45) Date of Patent: Feb. 18, 2025

(54) DRY EYE TREATMENT SYSTEM WITH DISPOSABLE TIP AND CORNEAL SHIELD

(71) Applicant: LUMENIS BE LTD., Yokneam (IL)

(72) Inventors: May Kleinman Ben Tsvi, Binyamina (IL); Yosef Birman, Haifa (IL); Hernan Altman, Kyriat Tivon (IL)

(73) Assignee: LUMENIS BE TLD. (IL)

( * ) Notice: Subject to any disclaimer, the term of this patent is extended or adjusted under 35 U.S.C. 154(b) by 38 days.

(21) Appl. No.: 18/074,765

(22) Filed: Dec. 5, 2022

(65) Prior Publication Data

US 2023/0165721 A1 Jun. 1, 2023

Related U.S. Application Data

(63) Continuation of application No. 17/506,795, filed on Oct. 21, 2021, now Pat. No. 11,540,949, which is a continuation of application No. PCT/IB2021/058217, filed on Sep. 9, 2021.

(60) Provisional application No. 63/076,485, filed on Sep. 10, 2020.

(51) Int. Cl.
*A61F 9/04* (2006.01)
*A61F 9/007* (2006.01)

(52) U.S. Cl.
CPC .......... *A61F 9/045* (2013.01); *A61F 9/00772* (2013.01); *A61F 9/0079* (2013.01)

(58) Field of Classification Search
CPC ..... A61F 9/045; A61F 9/00772; A61F 9/0079
USPC ........................................................ 128/858
See application file for complete search history.

(56) References Cited

U.S. PATENT DOCUMENTS

| | | | | |
|---|---|---|---|---|
| 4,570,626 A | * | 2/1986 | Norris | A61F 9/009 128/858 |
| 6,447,118 B1 | | 9/2002 | Okumura | C08K 3/22 351/159.33 |
| 2014/0090653 A1 | | 4/2014 | Clarke | A61F 9/007 128/858 |
| 2014/0371602 A1 | * | 12/2014 | Ito | A61B 5/0075 600/478 |
| 2015/0216725 A1 | * | 8/2015 | Korb | A61F 9/00718 606/171 |
| 2019/0299016 A1 | * | 10/2019 | Altman | A61N 1/40 |
| 2020/0170704 A1 | * | 6/2020 | Lukac | A61B 1/307 |
| 2020/0179168 A1 | * | 6/2020 | Kelleher | A61F 9/00718 |
| 2020/0360723 A1 | * | 11/2020 | Azar | A61H 5/00 |

FOREIGN PATENT DOCUMENTS

| | | | |
|---|---|---|---|
| CA | 2961391 | 9/2017 | ............... G02C 7/04 |
| JP | 2017533074 | 11/2017 | |
| WO | 2014179356 | 11/2014 | |

(Continued)

OTHER PUBLICATIONS

Search Report and Written Opinion—Corresponding PCT Application No. PCT/IB2021/058217, dated Feb. 10, 2022, 15 pages.

(Continued)

*Primary Examiner* — Aaron F Roane
(74) *Attorney, Agent, or Firm* — ISUS INTELLECTUAL PROPERTY PLLC; Anthony Jason Mirabito (57) ABSTRACT

A system for the treatment of the dry eye syndrome that is based on a light source. The system includes a disposable tip, to treat an eyelid. A corneal shield is used to protect the patient's eye.

15 Claims, 4 Drawing Sheets

(56) References Cited

FOREIGN PATENT DOCUMENTS

WO    2016070134    5/2016
WO    2018204903    11/2018

OTHER PUBLICATIONS

Invitation to Pay Additional Fees and Where Applicable, Protest Fee—Corresponding PCT Application No. PCT/IB2021/058217, dated Dec. 9, 2021, 10 pages.
Office Action—corresponding Japanese Application No. 2023-515804, dated Mar. 5, 2024, 7 pages.

* cited by examiner

DRY EYE TREATMENT SYSTEM WITH DISPOSABLE TIP AND CORNEAL SHIELD

CROSS-REFERENCE TO RELATED APPLICATIONS

This application is a continuation application of U.S. application Ser. No. 17/506,795, filed Oct. 21, 2021 which is related to and claims priority from U.S. Provisional Application Ser. No. 63/076,485 entitled DRY EYE TREATMENT SYSTEM WITH DISPOSABLE TIP AND CORNEAL SHIELD filed Sep. 10, 2020, which is incorporated by reference herein as if specifically set forth.

FIELD OF THE INVENTION

The present invention relates to a system for treating dry eyes using a disposable/removable tip, a corneal shield and a light source.

BACKGROUND

One main reason for dry eyes is blepharitis, a chronic inflammation of the eyelid margin. It has been shown that, for example, treatment with IPL (Intense Pulsed Light) light therapy or other has a long-lasting effect and bacteria and skin mites are successfully eliminated. The use of a light source is for the purpose of generating heat, and causing photo modulation, to heat up the area of a Meibomian Gland. Thus, other sources of generating heat other than light may be used.

In the course of treatment, several pulses of light may be delivered to a patient's eyelids. Care may be taken to avoid direct entry of light into the cornea, as well as exposing eyelashes to the energy to avoid hair loss. In addition, direct heating of the cornea and other ocular surfaces should be avoided.

SUMMARY OF THE INVENTION

One object of the invention is to eliminate or at least alleviate the problems discussed above.

The invention relates to a system for the treatment of dry eye syndrome of a patient. The invention comprises a light source, a controller for controlling the emission of light, a switch for triggering the treatment process, a fiber bundle connected or connectable to the light source, a disposable tip connectable to the fiber bundle, and a corneal shield for protecting the eye of a patient.

Another aspect of the invention is a corneal shield for use in the above-mentioned treatment system. The corneal shield is configured to prevent light energy from damaging the patient's eye. The shield comprises an outer surface, configured face in the direction of the light and an inner surface, adapted to face and conform to the shape of the cornea. The shield consists of a material which is flexible to prevent injury to or causing painful pressure on the cornea. It is also biocompatible and at least partly absorbs light energy.

Another aspect of the invention relates to a disposable/removable tip configured for use in above-described treatment system. The tip comprises a contact surface made of bio-compatible material that contacts the eyelid. The tip may have a distal end with a concave shape.

In an aspect, a corneal shield for placement on a patient's eye to protect the eye and its surrounding tissues during light treatment from a light energy source includes: a body having an outer surface (61), configured to be placed to face in the direction of the light energy source and an inner surface (62), configured in shape to the shape of the human cornea (8) and to be placed on the patient's cornea; wherein the shield is comprised of a flexible biocompatible material that is made of an at least partially light absorbing material. The biocompatible material may be one of silicon or a thermoplastic elastomer, and the material may be doped with $TiO_2$ (titanium (II)oxide). The corneal shield (6) may be doped with around 20% $TiO_2$.

In another aspect, the corneal shield material is doped with $TiO_2$ (titanium (II)oxide) configured to transmit less than 30% of the light energy, based on light energy from the light energy source onto the shield in the range of 5-20 $J/cm^2$. The corneal shield (6) may be a coated scleral contact lens coated with one or more layers of bio-compatible pigment. Further, the corneal shield may be coated with one or more coating layers applied on the surface of the shield that is configured to be placed in contact with the internal side of the patient's eyelid.

In yet another aspect, the corneal shield (6) may be a contact lens comprised of one or more materials to block treatment light. Further, the corneal shield (6) may be in the form of a scleral contact lens with a diameter generally in the range of 17-22 mm. The corneal shield may be in the form of a scleral contact lens coated on the outer layer (61) of the shield. The corneal shield (6) may be in the form of a scleral contact lens having more than one coating layers of a dark pigment. The contact lens may have more than one coating layers of a blue pigment. Also, the corneal shield (6) may be in the form of a scleral contact lens having one or more coating layers of a light pigment, further comprising a doping of $TiO_2$ to maximize the reflection of light. Further, the corneal shield (6) may be in the form of a scleral contact lens having one or more coating layers of a white pigment. The corneal shield (6) may be in the form of a scleral contact lens having one or more coating layers of a white pigment, wherein the layers are doped with $TiO_2$.

In an aspect, the corneal shield (6) is in the form of a scleral contact lens having more than one coating layers of a dark pigment and one or more coating layers of a light pigment. Further, the corneal shield (6) is in the form of a scleral contact lens having a plurality of pigmented coating layers in different orientations which provide a visual indication of the proper insertion of the contact lens into the patient's eye. The corneal shield (6) is in the form of a scleral contact lens having one or more reflective coating layers increasing the light reaching the surrounding tissues of the patient's eye.

In an aspect, a treatment system (10) for the treatment of dry eye syndrome of a patient includes: a light source (1); a source of vacuum or negative pressure; a controller (2) configured to control the emission of light and the source of vacuum or negative pressure connected to the light source (1) and the source of vacuum or negative pressure; a fibre bundle (4) connected to or connectable at its proximal end to the light source (1); an apertured disposable tip (5) connectable to the distal end of the fibre bundle (4) for contacting the outer surface the eyelid of an eye of the patient; a corneal shield (6) having and inner surface (62) and an outer surface (61) for protecting the eye (8) of a patient disposed between the light source (2) and the patient's eye; and a conduit in fluid communication with the source of vacuum or negative pressure to and through the disposable tip (5).

In another aspect, the treatment system (10) further includes a switch (3) connected to the controller, the switch configured such that when closed triggers the controller (2) to:
(1) cause the source of vacuum or negative pressure to be activated, whereby the disposable tip engages eyelid and pulls it away from contact with the cornea of the patient, and
(2) cause the light source to be activated to transmit light from the light source through the fibre bundle and through the apertured tip to impinge on the eyelid.

In a further aspect, the treatment system (10) characterized in that the controller (2) controls the light source (1) to emit a sequence of 3 pulses and delays, with a pulse duration of generally 6 ms each and a delay of generally 50 ms between light pulses. Further. The system (10) is characterized in that the system (10) further comprising an adapter for connecting the fibre bundle to a handpiece of a multi-function aesthetic treatment platform. Further, the fibre bundle (4) is connected with a pen-shaped handpiece (11) attached to the distal end (41) of the fibre bundle, said pen shaped handpiece having a switch (3) connected to the controller (2) that when closed triggers the treatment process.

In yet a further aspect, the corneal shield (6) is configured to prevent light energy from damaging the eye (8) of a patient, the shield (6) further comprising: an outer surface (61), configured to face in the direction of the light energy and an inner surface (62), adapted to the shape of the cornea (8). Further, the corneal shield (6) further includes one or more air-passage vents (64) through the outer (61) and inner surface (62). The corneal shield (6) further may include a handle (63) protruding from the outer surface (61) for manual handling of the corneal shield (6).

In an aspect, the corneal shield (6) further includes a handle (63) protruding from the outer surface (61) for manual handling of the corneal shield (6), said handle (63) having one or more air-passage vents (64) through the handle (63) from the outer surface (61) to the inner surface (62). The corneal shield (6) further may include a handle (63) protruding from the outer surface (61) for manual handling of the corneal shield (6), said handle (63) having one or more an air-passage slits (65) through the handle (63) from the outer (61) to the inner surface (62), further comprising an air-passage vent (64) disposed at one edge of the slit (65).

In another aspect, the corneal shield (6) further may include a handle (63) protruding from the outer surface (61) for manual handling of the corneal shield (6), said handle (63) having one or more air-passage vents (64) and or/slits (65) having a greater area within the handle than on the outlets (66) on the outer surface (61) and inner surface (61). The corneal shield (6) further may include, from the inner surface (62) to the outer surface (61), an air-passage vent (64) and/or slit (65) a greater cross-sectional area on the outlet (66) at the inner surface (62) than on the outlet (66) of the outer surface (61). The corneal shield (6) may have a generally dome shape, the open end being configured to be placed on the patient's eye.

In a further aspect, in the treatment system, the disposable/removable tip (5) may include: a contact surface made of bio-compatible material, configured to be in contact with the eyelid, further comprising a tip having a distal end with a concave shape.

BRIEF DESCRIPTION OF THE FIGURES

Some embodiments will be described in the following by way of example only, and with reference to the accompanying figures, in which.

DETAILED DESCRIPTION

Various embodiments will now be described more fully with reference to the accompanying drawings.

Figure 1:
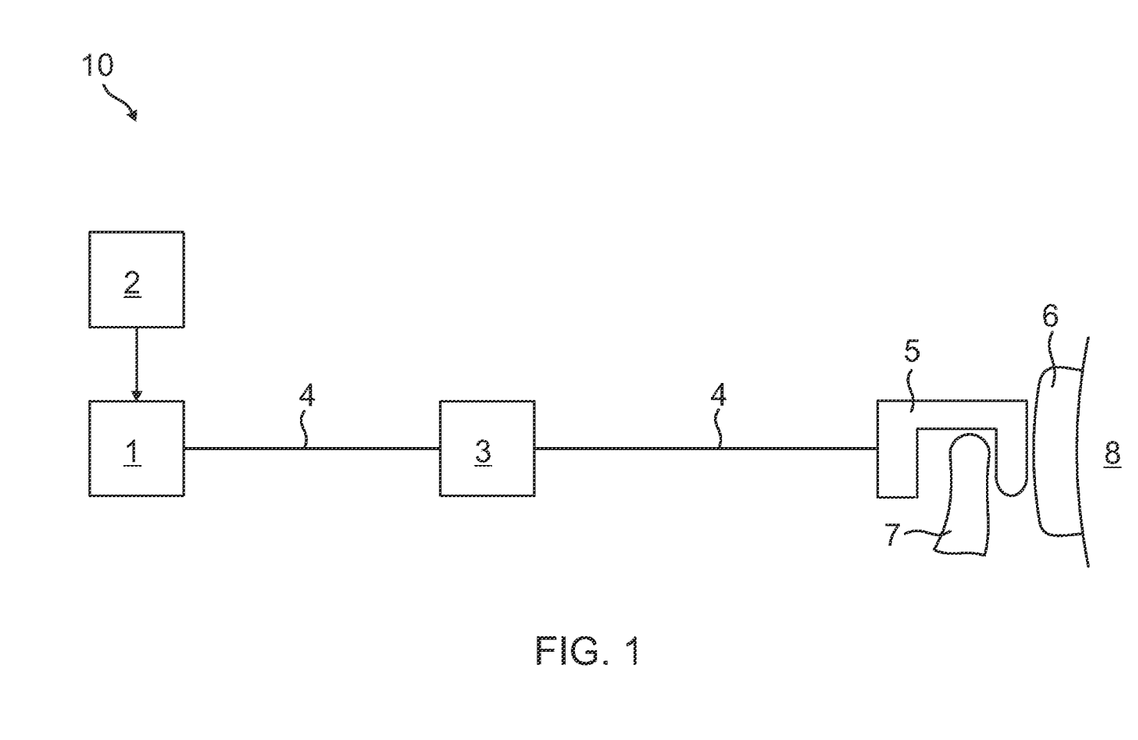
FIG. 1 shows a preferred embodiment of the treatment system for the dry eye syndrome.

FIG. 1 illustrates a treatment system 10 for the treatment with a light source 1 of a patient's dry eye syndrome source. The light source 1 is adapted to emit Intense Pulse Light (IPL), laser light or another type of light, such as light from one or more LEDs. A controller 2 is implemented to control the emission of light determines physical parameters of the light, such as the frequency or modulation of the light emitted by the light source 1. This can be done by controlling the light source 1 or interrupting or altering a steady emitted light by e.g., filtering the light from the light source 1.

According to a preferred embodiment, the controller 2 is configured to cause the light source to provide a several light pulses (Pulse sequence). One Pulse Sequence may for example consist of a train of 3 pulses. It has been shown that the duration (on-time) of a pulse is preferred to be 6 ms+/−20% and the delay (off-time) preferably is 50 ms+/−20%. Additionally, it has been shown that treating each eyelid 7 with 5-7 spots delivers especially good results, even more so in the event that the treatment is repeated for each eyelid twice per each eye, ideally in 2 runs. This results in about 40-50 pulses per treatment.

Depending on the skin types (according to the Fitzpatrick scale), these parameters may be optimized. The (maximum) fluence of energy without harming the skin depends on the skin type. The darker the skin type the lower the lower the fluence. For a darker skin type, the delay may increase from 50 ms to 100 ms for safety reasons.

The following data sets proved to be useful for a fluence value derived from the display of an Optima module LG plus disposable tip in $J/cm^2$:

Skin type I may be treated with a fluence of 14 $J/cm^2$, an OPT-type filter (590 nm), a triple pulse with a pulse duration of 6 ms and a pulse delay of 50 ms.
Skin type II may be treated with a fluence of 13 $J/cm^2$, a filter type of OPT (590 nm), a triple pulse with a pulse duration of 6 ms and a pulse delay of 50 ms.
Skin type III may be treated with a fluence of 12 $J/cm^2$, a filter type of OPT (590 nm), a triple pulse with a pulse duration of 6 ms and a pulse delay of 50 ms.
Skin type IV may be treated with a fluence of 11 $J/cm^2$, a filter type of OPT (590 nm), a triple pulse with a pulse duration of 6 ms and a pulse delay of 50 ms.
Skin type V may be treated with a fluence of 10 $J/cm^2$, a filter type of OPT (590 nm), a triple pulse with a pulse duration of 6 ms and a pulse delay of 100 ms.

An optional switch 3 for triggering the treatment process determines if light is sent to the treatment area, i.e., the eyelid 7. The switch 3 may be activated by the operator or physician. The switch 3 may be any type of control, e.g., also a graphical user interface.

During treatment, light is sent via a fiber bundle 4 which is detachably connected to the light source 1 on one side.

Figure 2:
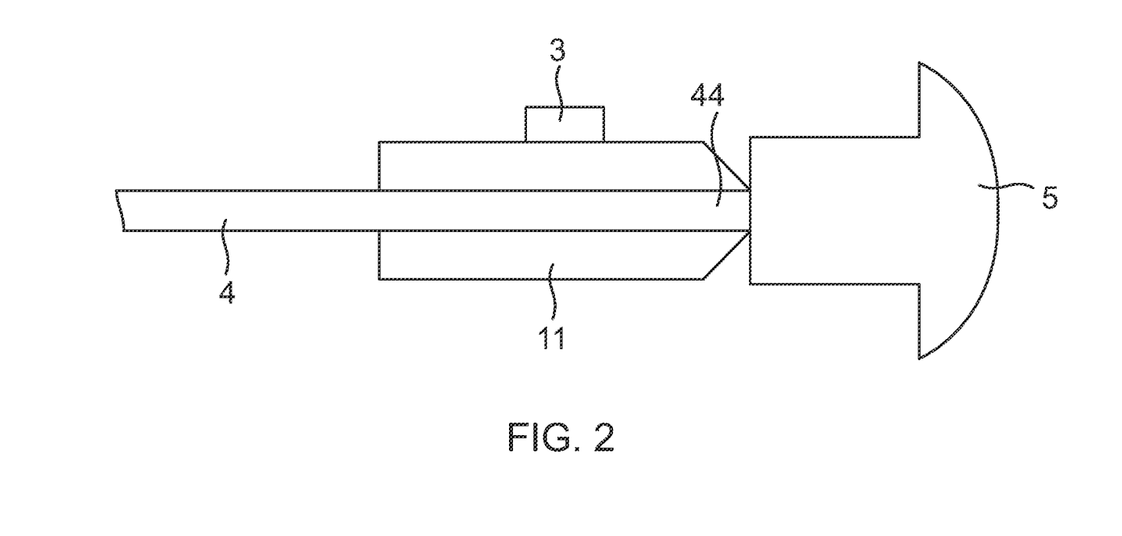
FIG. 2 shows an assembly of a fiber bundle, handpiece and disposable tip.

A disposable tip 5 is detachably connected to the distal end of the fiber bundle 4. The type of disposable tip 5 illustrated in this embodiment is of a clamping variety which holds the eyelid 7 in a bracket. Alternatively, a straight tip 5, as shown in FIG. 2, may also be used. Other types are also possible for use in the present system.

A corneal shield 6, for protecting the eye 8 of a patient, is positioned on the cornea. According to an embodiment where a clamping corneal shield is used, the corneal shield is positioned between the distal end of the disposable tip 5 and the cornea. However, according to an embodiment where a straight tip is used, the corneal shield is positioned between the back of the eyelid and the cornea.

FIG. 2 illustrates how the fiber bundle 4 is attached to a pen-shaped handpiece 11 at the distal end 41 of the fiber bundle. As mentioned above, a straight tip may be used in order to irradiate the eyelid by directing energy from its external surface only. The handpiece 11 may also comprise the switch 3 for triggering the treatment process. Alternatively, the switch 3 could be designed to be activated with the foot to provide hands free switching.

As the disposable tip 5 is attached at the distal end of the fiber bundle 4, the definition of the term "distal end 41" with respect to the handpiece means "at or close to the distal end 41".

FIGS. 3A to 3E illustrate different embodiments of the corneal shield 6. The purpose of the corneal shield is to prevent light energy from damaging the eye 8 of a patient during the treatment procedure The shield 6 has a dome-shaped form with an outer surface 61, facing the eyelid 7, and an inner surface 62, facing the eye 8.

The shield is adaptable to the shape of the eye/cornea 8. As eyes 8 of different patients differ in shape, the dome-shaped form or at least the inner surface 62 is accordingly adapted to the dimension of the eye of a patient. To adapt well to the individual eye 8 of a specific patient, the material of the shield 6 preferably is biocompatible and flexible in order to prevent from causing harm- or painful pressure to the cornea. Furthermore, the material could be autoclavable or the shield 6 could be disposable or for one-time use only.

The flexibility of the material allows or simplifies placing and releasing the shield 6 onto and from the eye 8 of a patient.

A corneal shield 6 is configured to protect the eye from the irradiated optical energy which is not absorbed by the eyelid, and at the absence of protection may penetrate and harm sensitive eye tissue. Metal or solid corneal shields known in the prior art may be totally opaque and block potentially harmful irradiation. However, such solid corneal shields tend to heat due to absorbed optical energy. This, in turns, may cause thermal damage to the cornea. A flexible corneal shield, which is disclosed in this disclosure as an aspect of the invention may be configured to optimize between its light energy absorption coefficient, opaqueness, and the thermal energy generated in the corneal shield material due to the light absorption. Light energy is at least partly absorbed by the corneal shield 6. It has shown that the ideal amount of absorption of the corneal shield is based on two factors: The amount of light energy, which (if not absorbed by the corneal shield) may harm the eye, and the amount of heat conducted via the corneal shield and generated by the absorption of light energy by the shield 6.

Surprisingly it has shown that a semi-transparent, or at least not fully opaque, corneal shield works best for the treatment and prevents from local potentially harmful heat peaks.

The material of the shield 6 may comprise or consist of silicon elastomer (e.g., 80 Shore A) or, alternatively, a thermo plastic elastomer. Especially preferred, the material of the shield is doped with $TiO_2$ (titanium (II)oxide), e.g., between 10 to 30% $TiO_2$, in particular 20% $TiO_2$.

The doping with $TiO_2$ is used as a chromophore to partly absorb the light energy and protect the eye. Without the chromophore doping, the elastomer or other material has only a poor absorption coefficient in the wavelength range of the light used, so that it does not get hot and does not risk the eye 8. The safety requirements applicable to lasers is more toward an absolute opacity due to the coherency of laser light. However, with IPL, since it is not a coherent light, some energy may still reach the eye without causing harm.

In one embodiment, the doping is configured to transmit 10-30% of the energy, based on an input light energy range of 5-20 $J/cm^2$.

Figure 3A:
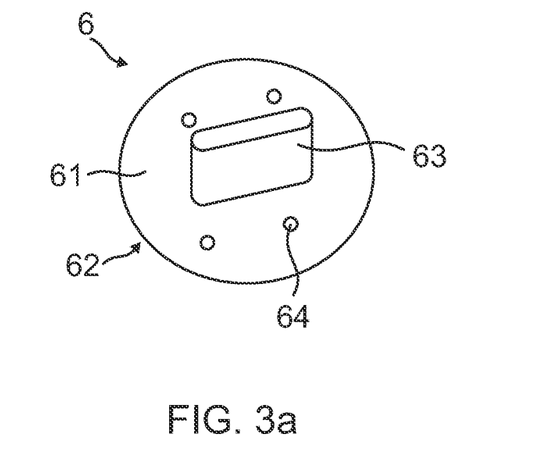
FIG. 3A shows a corneal shield with air-passage vents.

FIG. 3A illustrates one embodiment of the corneal shield 6, having a handle 63 protruding from the outer surface 61 for the purpose of handling the corneal shield 6. Handling is intended to be manual but handles 63 for machine placed shields 6 are possible.

At least one air-passage vent 64 connects the outer 61 and inner surface 62. The vents 64 may have a round shaped form, i.e., being a hole or aperture. The shield 6 in FIG. 3*a* comprises four vents 64, two on each side of the handle 63. The distances between the vents 64 might be equidistant, to provide equally distributed ventilation to prevent an unintended suction effect which leads to difficulties in removing the shield 6 from the eye 8 after conclusion of the treatment process. During removal of the shield 6 air may pass through the vents 64, allowing for easy removal of the shield, thus preventing or at least minimizing any potentially harmful forces being imposed on the eye 8.

Figure 3B:
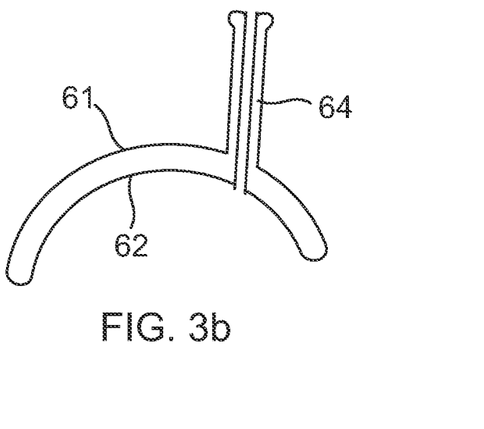
FIG. 3B shows a cross-sectional view of a corneal shield with an air-passage vent through the handle.
Figure 3C:
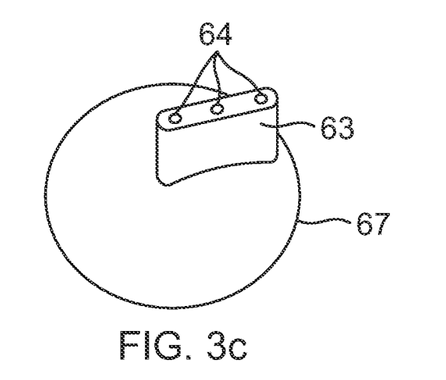
FIG. 3C shows a top view of a corneal shield with an air-passage vent through the handle.
Figure 3D:
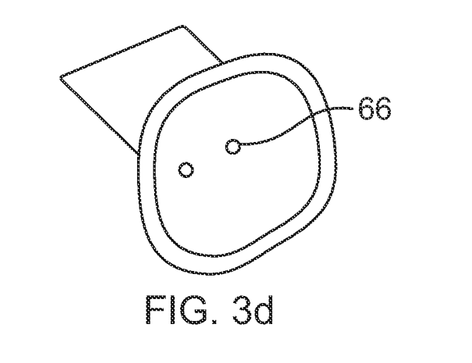
FIG. 3D shows a bottom view of a corneal shield with an air-passage vent through the handle.

FIGS. 3*b*, 3*c* and 3*d* illustrate other embodiments of a corneal shield 6. FIG. 3*a* is a cross-sectional view, where air-passage vents 64 lead through the handle from the outer to the inner surface instead of leading through the dome as shown in the embodiment of FIG. 3*a*. This allows a more centrally oriented ventilation and the possibility to block and unblock the airflow manually.

To prevent blockage of the airflow, three vents 64 or holes may lead through the handle, as illustrated in FIG. 3*c*.

Figure 3E:
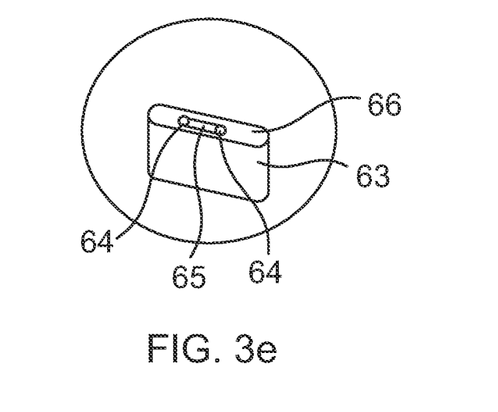
FIG. 3E shows a corneal shield with an air-passage slit through the handle.

FIG. 3*e* illustrates another embodiment of a corneal shield 6. An air-passage slit 65 leads through the handle 63 from the outer 61 to the inner surface 62. This allows passage of a larger air volume within the handle 63. This embodiment allows one to squeeze out even more air than with small holes as proposed in the previous embodiments.

As illustrated, an air-passage vent 64 is located on each side or edge of the slit 65. This cross-sectional form is configured to keep an open passage of ambient air toward the cornea even when the handle is held. This prevents unintentional blocking of the air-passage. When the handle of this embodiment is squeezed, the two opposite walls of the straight slit 65 come in contact, however, the two holes 64 at the edge of the slit 65 are wider in diameter than the slit 65 and accordingly the passage still remains open allowing a free flow of air and pressure equalization.

To further amplify the usability of the corneal shield, the cross-sectional area of the air-passage vent 64 and or/slit 65 within the handle 63 is greater than at the cross-sectional area of the orifices 66 of the outer 61 and/or inner surface 61. Thus, an additional air reservoir is provided in comparison with previous embodiments.

In a further preferred embodiment, the air-passage vent(s) 64 and or/slit 65 comprise a greater cross-sectional area 66 on the inner surface 62 than on the outer surface 61. This allows pumping more air towards the eye when the handle 63 is squeezed, i.e., the fingers hold and press the handle 63.

To release the corneal shield 6 from the eye 8, the handle 63 is squeezed to eliminate the suction effect, shortly before separating the shield 6 from the eye 8. Alternative measures in addition to the designing of the cross-sectional areas may be taken, e.g., a geometry which tends to let more air flow toward the cornea 8 rather the opposite side, when the handle 63 is compressed by the fingers.

In another embodiment, the air-passage vent(s) 64 and or/slit 65 provides a greater cross-sectional area on the outer surface 61 than on the inner surface 62. This allows pumping air away from the eye when the handle 63 is squeezed. This allows activation of the suction effect, when applying the shield 6 to the eye 8 and causing adhesion between both.

A combined embodiment, where pressing together one side produces a suction effect, and pressing on the other side other side produces a release effect.

While the foregoing is primarily in connection with a coated corneal shield, it is also envisioned, in another embodiment, that a scleral disposable contact lens, coated with one or more layers of bio-compatible pigment, may be implemented.

The general scleral contact lens geometry may be similar to that of a scleral lens. However, the external diameter may be relatively large as compared to a corneal lens, in the range of 17-22 mm, with a landing zone over the sclera (as compared to a typical corneal lens of are approximately 12-14 mm diameter). This is to ensure total coverage of the cornea, even during eye movements, to block IPL light. In addition, this allows for reduction of the contact between the shield and patient's cornea, while pressing the eyelid during IPL application.

Several coating layers (in the range of 2-5) are based on dark pigment (blue), to maximize blocking of light through absorption.

Additional coating layers (in the range of 1-2) are of a lighter color (white) including having doping of $TiO_2$, to maximize reflection of light.

This combination allows for maximal blocking, while reducing overheating of the shield, to avoid shield damage and/or eye thermal damage.

The reflective coating, in addition, allows for some of the IPL light to return toward the Meibomian glands from below the eyelid. This potentially improves the efficacy of the treatment, as the target organ is reached from a very short distance, Meibomian glands are located deep within the eyelid, posteriorly, and towards the eye conjunctiva.

The coating layers may be applied on the external surface of the shield, that is, the surface which is in contact with the internal side of the patient's eyelid. The internal surface of the shield is not coated. This internal surface is in direct contact with the eye/sclera. Since it is uncoated, the interface between the patient eye and the shield is identical to normal scleral contact lenses in terms of friction, biocompatibility, etc. and is proven to be safe.

Due to the use of two different coating pigments, the orientation (inside/outside) of the shield is clearly visible to the physician or other person performing the treatment, so the potential for mistakenly reversing the shield and misplacing it in error onto the eye is minimized if not completely eliminated.

The shield may be disposable. One embodiment uses the typical materials for single use contact lenses. The shield preferably may come in a sterile packaging, in which the shield is contained in a buffer solution (saline/water) to maintain its flexibility and sterility until used. Typical shelf life may be in the range of 1-3 yrs.

Figure 4:
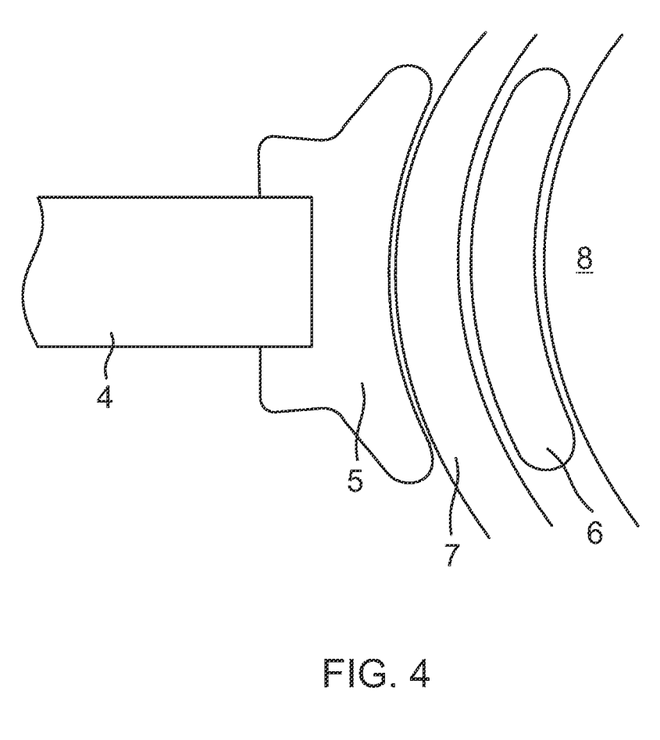
FIG. 4 shows an arrangement of the disposable tip and the corneal shield during the treatment.

FIG. 4 illustrates how a disposable/removable tip 5, connected to a fiber bundle 4, interacts with a corneal shield 6 during a treatment setting. The contact surface of the tip 5 is made of bio-compatible material, which allows contact with the eyelid 7. The shield 6 protects the eye 8.

Due to reasons of space and comfort, the shapes of the tip 5 and shield 6 should interact. The tip 5 may therefore comprise a concave shape at the distal end, which interacts/fits with the convex outer surface 61 of the corneal shield 6.

REFERENCE NUMBERS

1 light source
2 controller
3 switch
4 fiber (bundle)
5 disposable tip (DT)
6 corneal shield
7 eyelid
8 eye/cornea
10 treatment system
11 handpiece
41 distal end (of the fiber bundle)
61 outer surface
62 inner surface
63 handle
64 air-passage vent
65 air-passage slit
66 outlets/orifices

What we claim is:

1. A treatment system for the treatment of dry eye syndrome of a patient comprising:
    an intense pulsed light (IPL) source;
    a controller configured to control the IPL source;
    a fibre bundle detachably connected at its proximal end to the IPL source;
    a disposable tip detachably connected to a distal end of the fibre bundle and having a contact surface made of bio-compatible material configured for contacting the outer surface of the eyelid of an eye of a patient;
    a corneal shield comprised of a flexible biocompatible material doped with $TiO_2$ titanium(II)oxide) and having two or more layers of a blue pigment light absorbing material, and one or more layers of light reflective material; and
    the corneal shield configured for placement on a cornea of the eye to protect the eye during treatment with light from the IPL source.

2. The treatment system according to claim 1, comprising a switch connected to the controller, the switch being configured to trigger the controller to activate the light source to emit light through the fibre bundle and through the disposable tip to impinge on the eyelid.

3. The treatment system according to claim 2, comprising a pen-shaped handpiece to which the distal end of the fibre bundle is inserted, the switch being mounted on the pen-shaped handpiece.

4. The treatment system according to claim 1, comprising a pen-shaped handpiece to which the distal end of the fibre bundle is inserted.

5. The treatment system according to claim 1, wherein the disposable tip comprises the contact surface having a distal end with a concave shape.

6. The treatment system according to claim 1, wherein the disposable tip has a clamping configured to hold the eyelid in a bracket.

7. The treatment system according to claim 1, wherein the controller is configured to control the light source to emit a sequence of 3 pulses and delays between the pulses, each of the pules having a pulse duration of 6 ms and each of the delays extending between 50 ms to 100 ms between the pulses.

8. The treatment system according to claim 1, wherein the controller is configured to control the energy fluence from the light source, in a range between 10 J/cm$^2$ and 14 J/cm$^2$ based on skin type.

9. The treatment system according to claim 1, comprising an adapter for connecting the fibre bundle to a handpiece of a multi-function aesthetic treatment platform.

10. The treatment system according to claim 1, wherein the controller determines physical parameters of light emitted by the light source, including one or more of frequency and modulation of the light.

11. The treatment system according to claim 10, wherein the controller determines the physical parameters of the light by interrupting or altering the emitted light.

12. The treatment system according to claim 1, wherein the disposable tip comprises the contact surface having a distal end with a concave shape that fits with a convex outer surface of the corneal shield.

13. The treatment system according to claim 1, wherein the corneal shield is made from flexible biocompatible material comprising one or more of silicon and thermoplastic elastomer.

14. The treatment system according to claim 1, wherein the corneal shield comprises one or more air-passage vents passing through body of the corneal shield between outer and inner surfaces of the corneal shield body.

15. The treatment system according to claim 1, wherein the corneal shield comprises a handle protruding from outer surface of the corneal shield.

* * * * *